United States Patent
Baust et al.

[11] Patent Number: 5,916,212
[45] Date of Patent: Jun. 29, 1999

[54] HAND HELD CYROSURGICAL PROBE SYSTEM

[75] Inventors: John G. Baust, Candor; John M. Baust, Ithaca, both of N.Y.; Lawrence Pottorf, Charlestown; Roy Cheeks, Harpers Ferry, both of W. Va.; Hewu Ma, Rockville; Chao-Min Zhang, Gaithersburg, both of Md.; Alan F. Rich, North Reading, Mass.; Richard J. Reinhart, Lawrenceville, N.J.

[73] Assignee: Cryomedical Sciences, Inc., Rockville, Md.

[21] Appl. No.: 09/012,455

[22] Filed: Jan. 23, 1998

[51] Int. Cl.⁶ ..................................... A61B 17/36
[52] U.S. Cl. .............. 606/22; 607/104; 607/113
[58] Field of Search ............ 606/20–26; 607/96, 607/104, 107, 113; 62/293

[56] References Cited

U.S. PATENT DOCUMENTS

| | | |
|---|---|---|
| 3,886,945 | 6/1975 | Stumpf et al. . |
| 4,377,168 | 3/1983 | Rzasa et al. . |
| 5,451,208 | 9/1995 | Goldrath ................................. 604/55 |
| 5,603,221 | 2/1997 | Maytal ................................. 62/51.2 |

Primary Examiner—Beverly M. Flanagan
Assistant Examiner—Roy Gibson
Attorney, Agent, or Firm—Sherman and Shalloway

[57] ABSTRACT

The present invention relates to a portable, hand held, self-contained cryosurgical probe system. In particular, the present invention relates to an improved portable, hand held cryosurgical probe system having easily changeable probes and cryogen sources wherein the cryogen can be provided in precharged cylinders mountable on the hand held unit and/or supplied from remote sources and which is capable of serving a plurality of probes via a multiprobe adapter. The present invention provides the flexibility of easily changeable probes and cryogen sources in a lightweight hand unit whereby different cryogens may be employed at different stages within a procedure or the cryogens may be mixed to vary the effective freeze capacity of the device.

18 Claims, 4 Drawing Sheets

HAND HELD CYROSURGICAL PROBE SYSTEM

FIELD OF THE INVENTION

The present invention relates to a portable, hand held, self-contained cryosurgical probe system. In particular, the present invention relates to an improved portable, hand held cryosurgical probe system having easily changeable probes and cryogen sources wherein the cryogen can be provided in precharged cylinders mountable on the hand held unit and/or supplied from remote sources and which is capable of serving a plurality of probes via a multiprobe adapter. The present invention provides the flexibility of easily changeable probes and cryogen sources in a lightweight hand unit whereby different cryogens may be employed at different stages within a procedure or the cryogens may be mixed to vary the effective freeze capacity of the device.

BACKGROUND OF THE INVENTION

Cryosurgery is a well established surgical method which is useful in the treatment of many conditions and which involves the application of extreme cold to tissues to effect freezing of the tissues. The instruments used are, in general, of two types, the spray type wherein cold refrigerant is sprayed directly onto the tissue to be frozen, and the closed end cryotip type in which the refrigerant is delivered to a portion of the tip that is inserted into the tissue. In probe type instruments, as opposed to direct topical application of a cryogen, cryosurgery may include the introduction of a low boiling point refrigerant into the closed probe tip, gas expansion utilizing a Joule-Thompson effect, employing the latent heat of vaporization such as with freon, precooled gases and liquids, or thermoelectric cooling.

A preferred form of cryosurgery employs a closed end probe through which a low boiling point refrigerant or Joule-Thompson expansion fluid is circulated. Such a closed end probe confines the cryogenic fluid within the instrument rather than applying it directly to the tissues. In closed end probes, the cold generated by a cryogenic fluid is confined to the area of the probe tip where heat transfer occurs across the probe tip to the surrounding tissues to form an ice ball of frozen tissue.

Closed end probes are commonly used in systems wherein a remote source of cryogen or a refrigeration console is connected to the probe via a transfer hose. Examples of such probes and probe systems include U.S. Pat. No. 2,319,542, Hall, U.S. Pat. No. 3,272,203, Chato, U.S. Pat. No. 3,398,738 Lamb, et al., U.S. Pat. No. 3,425,419, Dato, U.S. Pat. No. 3,502,081, Amoils, U.S. Pat. No. 3,507,283, Thomas, Jr., U.S. Pat. No. 3,696,813 Wallach, U.S. Pat. No. 3,807,403, Stumpf, et al., U.S. Pat. No. 3,886,945, Stumpf, et al. U.S. Pat. No. 3,918,439 Zimmer, U.S. Pat. No. 4,211,231, Rzasa, U.S. Pat. No. 5,334,181, Rubinsky, et al., U.S. Pat. No. 5,520,682, Baust, et al., and U.S. Pat. No. 5,573,532, Chang, et al. These systems are necessarily bulky and not easily movable from one location to the other, nor are they well suited to use outside of a formal operating room or in minor surgical procedures due to their cost and maintenance requirements.

In contrast, open end, or spray type, tips are commonly used in less expensive and disposable hand held systems, generally for topical cryotreatments. Examples of these types of systems include U.S. Pat. No. 3,411,483, Canoy, U.S. Pat. No. 3,534,739 Bryne, U.S. Pat. No. 3,794,039, Kollner, et al., U.S. Pat. No. 3,823,718, Tromovitch, U.S. Pat. No. 3,901,241, Allen, Jr., U.S. Pat. No. 4,787,385, Pfistershammer, and U.S. Pat. No. 4,043,341, Tromovitch. Such devices are not suitable for use in procedures performed within the body due to the difficulty in controlling the amount of cryogen released and the effects of over spray on surrounding tissues.

Portable, hand held, closed end probe apparatus where a charge of cryogen is supplied from a reservoir are known. However, these devices tend to be limited in utility to small site applications such as in ophthalmic surgery. In many cases, the reservoir of cryogen is built into the device and is neither refillable nor replaceable necessitating that the entire apparatus be removed from the site and replaced if additional cooling is necessary when the cryogen runs out. Such devices are represented by U.S. Pat. No. 3,910,278, Crandell, et al., U.S. Pat. No. 3,951,152, Crandell, et al., U.S. Pat. No. 3,993,075 Lisenbee, et al., U.S. Pat. No. 3,524,446, Crump, et al., and U.S. Pat. No. 3,830,239, Stumpf, et al. In those cases where the reservoir within the tool is refillable, this requires the presence of a separate charging unit, as in U.S. Pat. No. 3,425,417, Kanabar, et al. and U.S. Pat. No. 3,434,477, Thomas, Jr. Devices which permit the replacement of cryogen reservoir have structures which require partial disassembly of the probe body in order to effect the removal of the empty reservoir and replacement with a fresh one or are of a size which renders such replacement difficult while the probe remains in place at the surgical site. Examples of these devices are shown in U.S. Pat. No. 2,746,264, Keyes, U.S. Pat. No. 3,259,131, Kanbar, et al., U.S. Pat. No. 3,343,544, Dunn, et al., U.S. Pat. No. 3,532,094, Stahl, U.S. Pat. No. 3,575,176, Crump, et al. and U.S. Pat. No. 3,933,156, Riggi.

Absent from the prior art is any suggestion of a portable, hand held, self-contained cryosurgical system having the capability of handling a plurality of cryogens either individually or simultaneously. Nor is there any suggestion of such a system which has the capability of being connected to and using cryogen from a remote source, such as a refrigerating console or an auxiliary tank, simultaneously with a changeable, self contained source of the same or a different cryogen and where the surgeon can readily switch from one cryogen to the other or use a mixture of the two. Furthermore, the prior art hand held systems are limited to use with one probe at a time probe, there being no provisions for mounting multiple probes to one device.

One patent, U.S. Pat. No. 4,376,376, Gregory discloses a cryogenic device operable in single or dual phase and with a range of nozzle sizes. This patent presents an open-nozzle spray type device in which a liquid cryogen stored in a hand held Dewar is supplied through an orifice into an expansion chamber on which a nozzle is mounted. A pressurized gas from a pressure regulated gas source is supplied to the device as a means to control gas pressure in the expansion chamber and the Dewar and to provide a single phase gas flow or a dual phase gas and liquid flow to the nozzle. The pressurized gas flow serves to maintain a stable flow of the liquid cryogen from the Dewar by combined manipulation of a venting passage and gas flow pinch valve. The pressurized gas also serves to pressurize the Dewar to ensure proper flow of liquid cryogen to the expansion chamber. Thus, although the Gregory device discloses selective single or dual phase flow of cryogen, it is not possible to achieve the dual phase absent the application of the pressurized gas and single phase flow. Furthermore, there is no provision for use of the apparatus with closed tip cryoprobes or with multiple probe systems.

Another drawback to the prior art portable, hand held cryosurgical devices occurs when the area to be treated is too large or irregularly shaped to be totally destroyed by only a single probe tip. It often happens that the size and shape of a tumor being treated is not fully recognized until after surgery begins. Also, it is not uncommon for a surgeon to find multiple tumors during surgery. With only a single cryosurgical instrument probe, the surgeon cannot always efficiently or safely treat large or multiple tumors. In the larger console type cryosurgical systems this problem has been solved by providing a manifold in the console which has a plurality of ports for connection of probe hoses such as in U.S. Pat. No. 2,319,542 and U.S. Pat. No. 5,334,181. However, no manifold system has been devised for use with portable hand held probes which have a self carried source of cryogen and, particularly, where the structure of the prior probe units are such that it is not possible to use a plurality of probes having self contained cryogen sources in close proximity with each other. Moreover, known hand held units are not designed to be capable of handling more than one probe at a time.

SUMMARY OF THE INVENTION

It is an object of this invention to provide an improved hand held cryosurgical system which combines the capabilities of larger console type systems with the portability of a hand held apparatus.

It is a further object to provide a hand held cryosurgical system which comprises an apparatus having the capability of operating as a completely self contained system or in combination with remote sources of cryogenic fluid.

It is a still further object to provide a hand held cryosurgical system having the capability of simultaneously feeding a plurality of cryoprobes.

And it is a still further object to provide a hand held cryosurgical apparatus which is readily adaptable and capable of handling different cryogens and sizes of cryoprobes for use in treating different types of tissues in different locations within the body.

Further objects and advantages will become evident from the following description and drawings.

The present invention provides a hand held cryogenic apparatus comprising a body of thermally insulative material having a first quick disconnect coupling connectable to a source of a first cryogen, a second quick disconnect coupling connectable to a source of a second cryogen, a third quick disconnect coupling connectable to a cryoprobe member. Within the apparatus a first conduit extends from the first coupling and a second conduit extends from the second coupling, the first and second conduits joining adjacent and connecting to the third coupling to convey cryogen from the first and second source. The first and second conduits each have separately controllable valve means therein to provide individual flow control within the conduits allowing for separate flow of each cryogen or a variable combined flow. A cryoprobe member connectable to the third coupling has means to receive and circulate the cryogens therethrough and a vent means is connected to the third coupling and exits from the body to vent spent cryogen from the cryoprobe member.

The present invention further provides a portable cryosurgical probe system comprising a hand held cryoprobe apparatus comprising a body having means to changeably receive a cryoprobe member, means to changeably receive a container of cryogen, means to removably connect the apparatus to a second source of cryogen, means within the body to convey cryogen from the container to the cryoprobe member and from the second source of cryogen to the cryoprobe member, vent means to exhaust spent cryogen from the apparatus, and means to control flow of cryogen through the apparatus. The system includes at least one container of cryogen removably mountable to the body and at least one cryoprobe member removably mountable to the body to receive cryogen flow. In addition, an adapter member is provided which is mountable to the body in place of a single cryoprobe and which includes a plurality of hoses and probes as well as a means to divide the cryogen flow from the body to the plurality of probes.

In addition, the present invention provides an adapter member for use with the portable, hand held cryogenic apparatus and system which adds the capability of simultaneously using multiple cryoprobes with the hand held unit.

The present invention still further provides a method of conducting a cryosurgical procedure on selected tissue in the human body using a hand held, self-contained cryosurgical apparatus, which method comprises:

providing a cryosurgical apparatus comprising a body of thermally insulative material having a first coupling for quickly connecting and disconnecting to a source of a first cryogen, a second coupling for quickly connecting and disconnecting to a source of a second cryogen, a third coupling for quickly connecting and disconnecting to a cryoprobe member, a first flow passageway extending from said first coupling and a second flow passageway extending from said second coupling, said first and second flow passageways joining adjacent to said third coupling and connecting to said third coupling as a single passageway, said first and second flow passageways each having separately controllable valves therein, and a cryoprobe member connectable to said third coupling and having means to receive and circulate said cryogens therethrough, whereby said first and second flow passageways convey cryogen from said first and second sources to said cryoprobe member and said valves separately control the flow of said first and second cryogens providing individual flow of each fluid or combined flow thereof;

providing a cryoprobe member and mounting said member to said apparatus via said third coupling;

providing a cylinder of pressurized cryogen, said cylinder having a body and a neck portion wherein said neck portion has a structure to cooperatively seal with said first coupling and connecting said cylinder to said first coupling whereby said cylinder comprises said source of a first cryogen and whereby said cylinder is sized to be removably supported by said apparatus;

and positioning said cryoprobe member at said selected tissue and activating said valve in said first flow passageway whereby cryogen is caused to flow from said cylinder into said cryoprobe member and to generate freezing temperatures therein, said freezing temperatures being transferred to said tissues, and wherein, upon exhaustion of said cryogen in said cylinder, said cylinder is quickly removable from said apparatus and a second cylinder is connectable to said first coupling whereby said procedure continues uninterrupted

DETAILED DESCRIPTION OF THE INVENTION

The present invention solves the problems presented by the prior art in a cryosurgical apparatus which combines the portability and ease of use of the small, hand held, self-contained cryoprobes with the extended use and multiple cryogen capabilities of the larger console type systems. Toward that end, the invention comprises a hand held cryoprobe unit having fittings for removably receiving or connecting to a plurality of sources of cryogen and separate control means for regulating the flow of cryogen through the unit to a cryoprobe mounted thereon.

For use as a fully portable, self-contained system, the cryogen sources are preferably cylinders or Dewars having about a nine ounce volume and precharged with a pressurized gas or liquid such as nitrogen, freon, carbon dioxide, or other fluid which, when allowed to expand through a cryoprobe produces a degree of cold which is transmitted through the probe into the surrounding tissues. The nature of the fittings on the apparatus is such that the cylinders are readily and easily changeable during a cryosurgical procedure without removing the probe from the tissue. In this manner, the cooling ability of the device is extendable for as long as necessary without interrupting the procedure.

Alternatively, the apparatus may be connected to a remote source of cryogen, such as from a large size tank or a console type cryogen/refrigeration system providing greater cooling capacity, recirculation of cryogen, sub-cooling of cryogen, and the like. In addition, since the apparatus has at least two separate connections for cryogen sources, it is possible to combine two different cryogens in any ratio, or to alternate separate cryogens or a cryogen and a warming fluid, in addition to applying a single cryogen, whether the apparatus is used in a self-contained mode or in combination with a remote source of cryogen. Furthermore, by providing separate flow controls for each cryogen feeding into the apparatus, the range and freeze capacity of the apparatus is increased.

In addition, the invention provides an adapter for use with the apparatus whereby a plurality of cryoprobes are connectable to the hand unit for use in those situations requiring simultaneous cooling with more than one probe. In this manner, the multiprobe capability of larger systems such as Hall, U.S. Pat. No. 2,319,542, and Rubinsky, et al., U.S. Pat. No. 5,334,181, is brought to portable systems.

Figure 1:
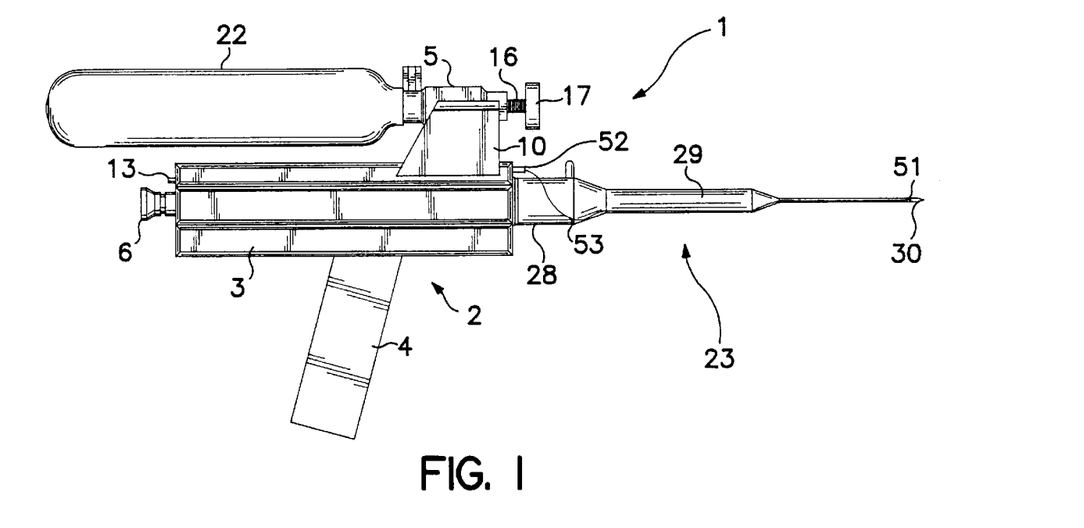
FIG. 1 is a side view of the hand held cryosurgical apparatus of the invention showing a cryoprobe member and cryogen cylinder mounted on the hand unit.

The portable hand held cryosurgical apparatus 1 of this invention is illustrated in FIG. 1 and comprises three elements, hand unit 2, pre-charged cylinder of cryogen 22, and cryoprobe 23. The arrangement of these elements is such that the balance of the apparatus renders it comfortable and easy to use.

Hand unit 2 comprises body 3 which is a substantially rectangular block of thermally insulative material with handle 4 extending downwardly from one side. Preferably body 3 and handle 4 are molded or milled from a light weight, thermally insulative plastic material such as polypropylene, polystyrene, polytetrafluoroethylene, fiber reinforced polymers, and the like. On the upper surface of body 3 is first coupling 5 which receives cylinder 22. Preferably first coupling 5 employs a mechanism which facilitates ease of changing from one cylinder to another during a cryosurgical procedure. Typically, since cylinders are produced with threaded necks 26, a threaded mechanism in first coupling 5 would be within the scope of this invention. However, other quick disconnect mechanisms may also be used such as bayonet connectors, detent mechanisms employing a spring-loaded retaining collar such as are commonly used on hoses, and the like. One such quick disconnect coupling which is commonly known comprises a male member having a peripheral groove and a female member or socket which receives the male member and which includes a plurality of balls which engage the peripheral groove and are held in locking position by a sleeve. The sleeve is slidable in an axial direction against a spring bias to a position in which the balls are permitted to move radially outwardly and thereby release the male member from the socket. A peripheral sealing gasket is provided within the female socket against which the male member seats when held in place by the balls to provide a seal in the coupling and prevent leakage. In the event this type of coupling is employed, it is preferred that coupling 5 comprise the female member and that cylinder 22 be formed with a neck 26 corresponding to the male member.

The principal requirement for first coupling 5 is that it receive and hold cylinder 22 and that it provide a leak-free connection with cylinder 22. First coupling 5 is supported by support member 10 which is attached to body 3 and also supports cylinder 22 when it is in place.

First coupling 5 includes a means to puncture the seal 27 of cylinder 22 to permit flow of cryogen from cylinder 22 into body 3 and to cryoprobe 23. This puncturing means may be a simple screw 16 having a puncturing point 24 which is driven into seal 27 of cylinder 22 by turning knob 17. Alternatively, puncturing point 24 may be fixed within the socket of coupling 5 such that the act of inserting and seating cylinder 22 in place drives seal 27 against the fixed point 24.

Figure 2:
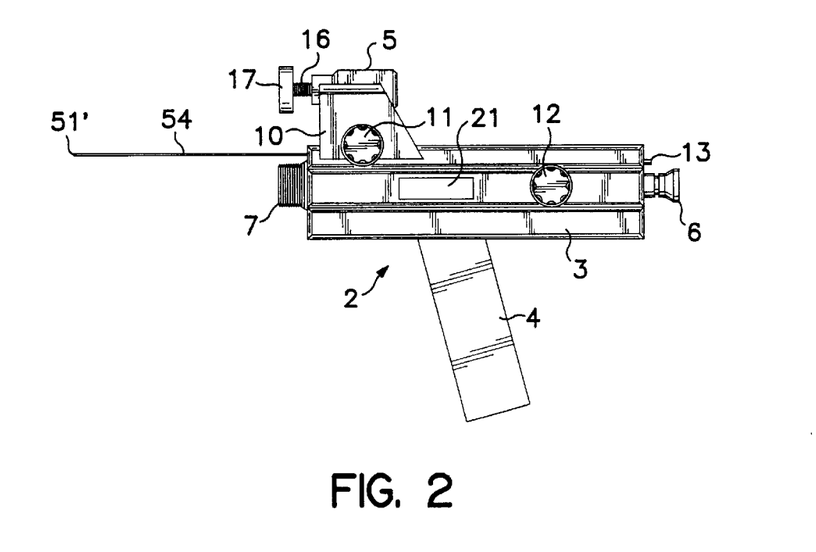
FIG. 2 is an opposite side view of the hand unit of the invention.

At the rearward end of body 3 is second coupling 6 which may be of the same type as first coupling 5 or of a different type. In the preferred embodiment shown, second coupling 6 is a quick disconnect type to receive the connector of a hose from a second source of cryogen. This source may be a large, substantially stationary cylinder of pressurized gas, such as liquid nitrogen, freon, or other cryogenic gas, or it may be a refrigerated liquid or subcooled cryogen provided by a refrigeration unit or console cryosurgical unit. As with first coupling 5, second coupling 6 must provide a leak-free connection to the second source of cryogen.

In an alternative embodiment of the apparatus, first and second couplings 5 and 6 are both designed to receive portable cylinders 22 in which case second coupling 6 is provided with a seal piercing means similar to that of coupling 5 to puncture the cylinder seal 27. This embodiment provides a fully self-contained apparatus which is capable of handling two separate sources of identical or different cryogens.

Figures 3, 4, 5:
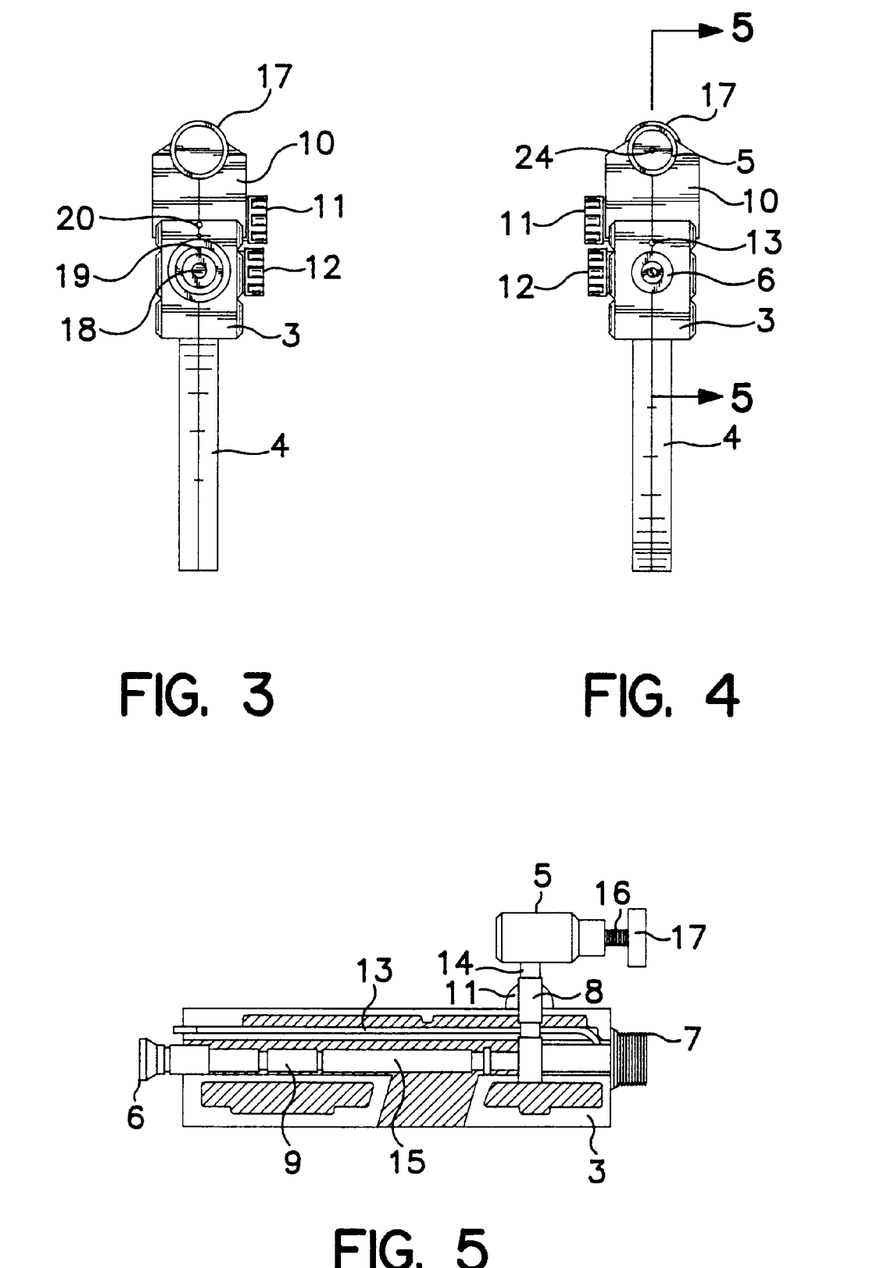
FIG. 3 is a front end view of the hand unit.
FIG. 4 is a rear end view of the hand unit.
FIG. 5 is a cross section of the body of the unit taken along line A—A of FIG. 4.

At the forward end of body 3 is third coupling 7 which removably receives cryoprobe 23 and provides a leak free seal therewith. Third coupling 7 may be a threaded coupling or a quick disconnect coupling as previously described and includes a cryogen inflow port 18 which connects to the cryogen flow line within cryoprobe 23, and a cryogen exhaust port 19 which receives spent cryogen from cryoprobe 23 and connects to vent 13 to exhaust spent cryogen from the apparatus. Vent 13, exhausts the cryogen to the atmosphere or it may be connected to a cryogen recovery unit. Preferably vent 13 exits body 3 at the rear adjacent to second coupling 6, but other exit points are possible.

Looking at FIG. 5 which is a cross section of body 3 taken along line A—A of FIG. 4, it is seen that second coupling 6 is connected to third coupling 7 by conduit 15 while first coupling 5 is provided with first conduit 14 which connects to second conduit 15 within body 3. First and second conduits 14 and 15 convey cryogen from first and second couplings 5 and 6 to third coupling 7. In order to control the flow of cryogen each conduit is provided with a valve 8 and 9 having controlling knobs 11 and 12.

Necessarily, valves 8 and 9 are functional through a wide range of temperatures including the extreme cold produced by cryogens such as liquid nitrogen. Any structure which will provide a variable flow control of such cold fluids may be used. One particularly suitable valve structure is a cryogenic needle valve in which a needle valve element cooperates with a seat to provide a flow control orifice. Each needle valve element is operated by a control knob. In a further embodiment, valve 8 and 9 are provided with flow rate sensors to measure cryogen flow from each source. Flow rate information is useful in controlling the freeze/thaw rate and in adjusting the mixture when two different cryogens are used with the apparatus.

Cryoprobe 23 is preferably a closed tip probe such as that disclosed in commonly assigned U.S. Pat. Nos. 5,254,116, 5,520,682 and 5,573,532, the disclosures of which are incorporated herein by reference. The probe comprises mounting collar 28 which houses a mounting means corresponding to and cooperating with third coupling 7. Within mounting collar 28 are the cryogen supply and exhaust tubes of cryoprobe 23 which cooperate with the inflow and exhaust ports 18 and 19 of third coupling 7. Extending from mounting collar 28 is cryoprobe body 29 which tapers down to probe tip 30.

In order to monitor the temperature of the tissue being frozen, the apparatus preferably includes a thermocouple 51 and a display means 21. The thermocouple 51 may be built in as part of the probe tip 30 or provided as a separately attachable element positionable on probe tip 30. A plug 20 is provided in the forward end of body 3 and is electrically connected to display means 21. Thermocouple 51 includes a corresponding plug 52 on the end of conductor 53 which removably connects to plug 20 for attachment of the thermocouple to display means 21. In an alternative embodiment, the thermocouple 51' is mounted on extendable probe 54 which is variably extendable from and retractable into body 3 linearly parallel to cryoprobe 23. In this embodiment thermocouple 51' is preferably directly connected to display means 21 through extendable probe 54. Display means 21 includes circuitry necessary to convert signals from thermocouple 51 and 51' to a visually readable display of temperature and a power source, preferably an easily replaceable battery. Controls are also provided as part of display means 21 for executing functions such as on, off, reset, mode change and the like.

In its preferred form, display means 21, is a digital display such as a liquid crystal or light emitting diode (LED) array. However, other digital or analog displays capable of providing a reading of time and temperature may also be used.

Liquid crystal systems are preferred due to their low power requirements and the ease of switching from one display mode to another. Although shown as an integral part of hand unit 2, display means 21 may be separate form hand unit 2 or designed to be removably mountable on hand unit 2. To that end, display means 21 is preferably a self contained unit in itself with respect to its circuitry, power source and controls. In addition to providing a display of temperature as measured by thermoprobes 51 and 51', display 21 preferably includes a mode for the display of time which may be standard time or elapsed time for a particular procedure or use of the apparatus. Also, where valves 8 and 9 include flow rate sensors, these are preferably connected to display 21 to provide the surgeon with a readout of cryogen flow rates.

Figure 6:
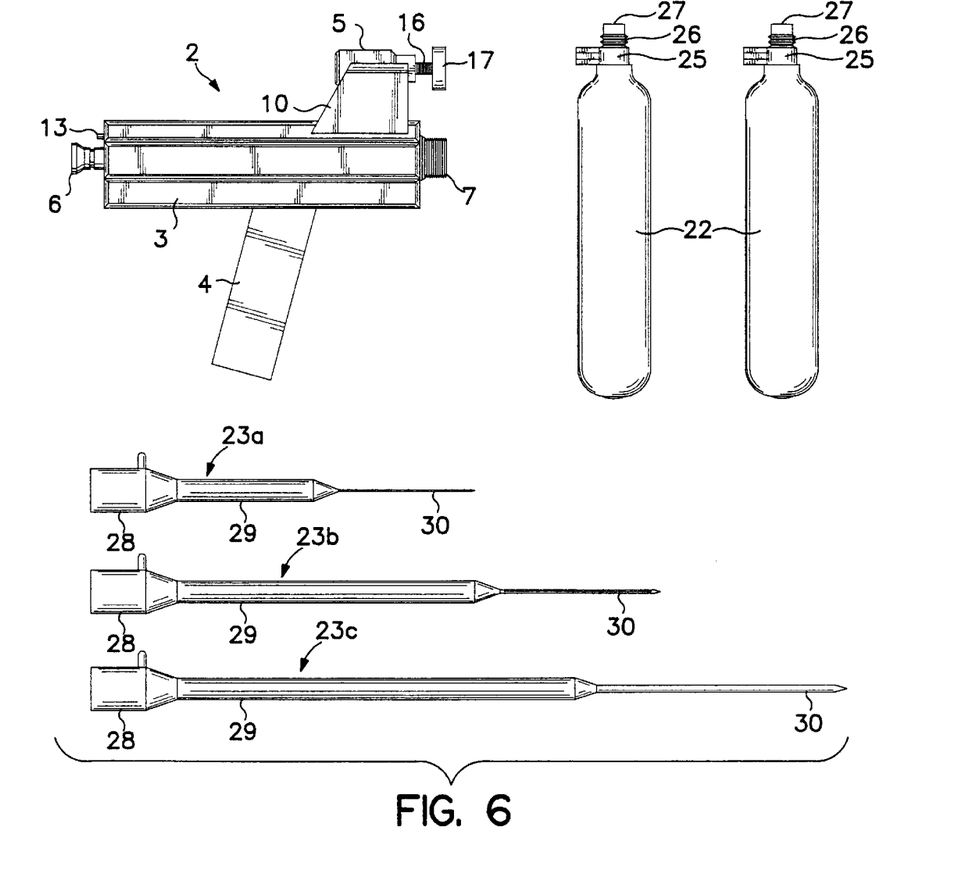
FIG. 6 is a collective view of the elements of the hand held cryosurgical probe system of the present invention.

In a preferred embodiment, shown in FIG. 6, the apparatus of this invention is provided as a system comprising hand unit 2, at least two precharged cylinders 22 of cryogen, and a set of cryoprobes 23a, 23b, and 23c, varying in size. The cryoprobe sizes shown correspond to 2 mm, 3 mm and 8 mm diameter probes; however, other sizes may be included or substituted without departing from the scope of the invention. In addition, systems may be provided with more than two precharged cylinders of cryogen. Furthermore, the system may be provided with cylinders of different cryogen, for example, separate cylinders of liquid nitrogen and freon may be included providing the surgeon with the capability of obtaining different freezing temperatures.

The apparatus with a variety of sizes of cryoprobes is useful for procedures conducted through natural and artificial body openings where prior art self contained units are not suitable, for example, gynecological, rectal and transurethral procedures. In gynecological procedures, the apparatus with a single cylinder and an 8 mm probe is well suited to the treatment of cervical tumors by freezing. The cryoprobe provides sufficient length to reach the site of the tumor while the rest of the apparatus remains comfortably outside the patient giving the surgeon ample room to adjust and maneuver while the actual freezing point is limited to the tip of the probe and is therefor able to be accurately placed at the site of the tumor without damaging surrounding tissue. At the conclusion of the freezing cycle, thawing may be accomplished by reducing the flow of cryogen or by substituting a source of warming fluid. Throughout this procedure, thermocouple 51 may be used to monitor the temperature of the freezing tissue. Alternatively, extendable probe 54 with thermocouple 51' may be used to monitor the temperatures of adjacent surrounding tissues to ensure that freezing does not extend into and damage healthy tissues.

Although the apparatus has been described in combination with closed tip cryoprobes, the ability to use different cryogens and the changeability of cryoprobes also enables the surgeon to use open tip, or spray type probes and cryogens appropriate thereto.

Figures 7, 8, 9:
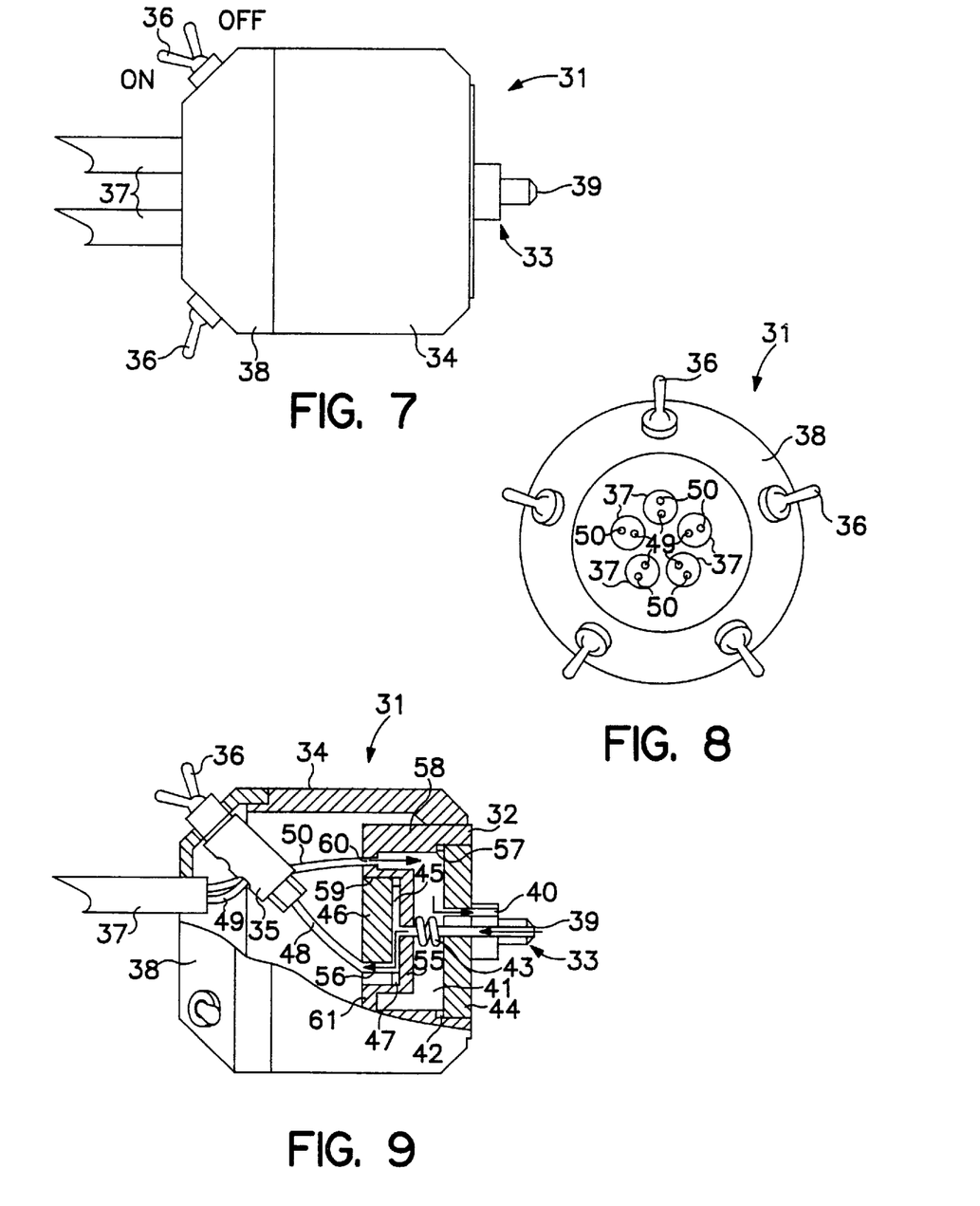
FIG. 7 is a side view of a multiple probe manifold adapter for use with the hand held cryosurgical probe system of the present invention.
FIG. 8 is a front view of the multiple probe manifold of FIG. 7.
FIG. 9 is a partial cross section of the multiple probe manifold of FIG. 7.

In addition to the hand unit 2, cylinders 22 and cryoprobes 23, the apparatus includes multi-probe adapter 31 which is mountable on third coupling 7 and provides a manifold structure which permits hand unit 2 to be used with and feed cryogen to a plurality of cryoprobes. FIGS. 7, 8 and 9 illustrate adapter 31 which comprises a housing 34 which is preferably substantially cylindrical. A first end of housing 34 is provided with a connector 33 which cooperates with third coupling 7 on hand unit 2 to mount adapter 31 thereon while hoses 37 feeding individual cryoprobes emanate from the second end of housing 34. Each hose 37 is provided with a probe feed conduit 49 and an exhaust conduit 50 and terminates in a fitting to receive a cryoprobe 23 or is preassembled with the cryoprobe in place and permanently attached. Like cryoprobes 23, connector 33 provides a leak-free seal between adapter 31 and third coupling 7 and includes inlet port 39 and exhaust port 40 which cooperate with cryogen inflow port 18 and cryogen exhaust port 19 of coupling 7.

Within the first end of housing 34 is manifold block 32 which defines separate inlet manifold chamber 45 and exhaust manifold chamber 41. Manifold block 32 is preferably formed as one piece with inlet manifold chamber 45 recessed within exhaust manifold chamber 41 and separated therefrom by wall 55. Exhaust manifold chamber is closed at the first end of housing 34 by exhaust port block 44 which seals against O-ring 42 which fits against annular shoulder 57 recessed in the sidewall 58 of exhaust manifold chamber 41. Inflow port 39 and exhaust port 40 pass through exhaust port block 44. A conduit connects inflow port 39 with inlet manifold chamber 45 through wall 55 and forms inflow coil 43 where it passes through exhaust manifold chamber 41. In this manner, cryogen entering adapter 31 from hand unit 2 is able to recapture remaining cold from exhausting cryogen passing out of adapter 31 through exhaust manifold chamber 41.

Inflow coil 43 delivers cryogen to inlet manifold chamber 45 through wall 55. Inlet manifold chamber 45 is closed by inlet manifold block 46 sealing against O-ring 47 which fits in the annular corner formed by wall 55 and the sidewall 59 of inlet manifold chamber. Inlet manifold block 46 is provided with a plurality of apertures 56 corresponding to the number of hoses 37 emanating from adapter 31. Each manifold aperture 56 is connected to a valve 35 by a conduit 48. Valve 35 may be a simple on-off valve, such as a toggle valve, to control the flow of cryogen into probe feed conduit 49 of each hose 37. Alternatively, valves 35 may be variable, such as needle valves. Each valve 35 has its own control switch 36 positioned on the second end of housing 34 adjacent to the hose 37 to which it is connected. Indicia may be provided on housing 34 to visually indicate when valve is on or off. Each hose 37 also includes an exhaust conduit 50 which conveys spent cryogen from the probe to exhaust manifold chamber 41 through exhaust apertures 60 in the backwall 61 of manifold block 32 for passage through exhaust port 40 into vent 13 of hand unit 2.

In operation as a self-contained unit, the apparatus is assembled with a cylinder 22 of cryogen mounted to first coupling 5 and cryoprobe 23 mounted to third coupling 7. With valves 8 and 9 closed, the puncturing means is operated by turning knob 17 to puncture the cylinder seal 27 thereby initiating cryogen flow.

With thermocouple 51 connected to display 21 and display 21 activated, cryoprobe 23 is inserted into the tissue to be treated until probe tip 30 is properly located. Valve 8 is opened by turning knob 11 to allow cryogen to flow into cryoprobe 23. Cryogen flow is adjusted through valve 8 until the desired flow rate indicated by the temperature reading from thermocouple 51 is achieved. Alternatively, if a flow rate measuring means is incorporated into the device, the display 21 may be configured to provide a visual indication of cryogen flow rather than or in addition to temperature.

When additional cooling is required, cylinder 22 is easily replaced with a fresh cylinder or a second cylinder is mounted to second coupling 6 and valve 9 is opened. This may be accomplished without thawing cryoprobe 23 and removing it from the tissue since body 3 and handle 4 provide sufficient structure by which the apparatus may be grasped and held while cylinders are changed or mounted. If a mixture of two types of cryogens is desired in order to achieve a particular thermal effect, one cryogen is fed through first coupling 5 and a second cryogen is fed through second coupling 6 with the mixture of the two being adjusted by controlling the flow of each cryogen through the respective valves 8 and 9.

When other sources of cryogen are available, such as from a console system, they are connectable to hand unit 2 by attaching feed hoses from the source to first and second couplings 5 and 6. Alternatively, a precharged cylinder 22 is connected to one coupling, preferably first coupling 5, and a hose from a second cryogen source is connected to the other coupling, preferably second coupling 6. As before, the rate of cryogen flow from each source is separately controlled by valves 8 and 9.

In procedures requiring the simultaneous use of multiple cryoprobes, such as prostate surgery, adapter 31 is employed. Although adapter 31 may be constructed with any number of hoses, limited only by the size of adapter 31, most procedures can be successfully completed using up to eight probes. Hence adapters 31 with five or eight hoses are preferred. In these procedures, the locations for probe placement are determined and appropriate cannulas are implanted into the patient providing multiple paths to the tissue. Cryoprobes 23 of the desired size are connected to the ends of each of the hoses 37 of adapter 31 and one probe is inserted through each cannula into the tissue to be frozen. With switches 35 in their off or closed positions, adapter 31 is mounted to third coupling 7 of hand unit 2. If the apparatus is being used as a self-contained unit, precharged cylinders 22 are preferably mounted to hand unit 2 before attaching adapter 31. Similarly, if cryogen feed is from a remote source, appropriate feed hoses from the source are first connected to couplings 5 and/or 6. With adapter 31 assembled to hand unit, valves 8 and 9 are opened to initiate cryogen flow, followed by turning of valves 35 to their on position for those hoses 37 being used to supply cryoprobes. The valve 35 for any hose 37 not being used will remain closed.

Valves 35 may be opened substantially simultaneously to commence cryogen flow through all of the hoses at the same time or the operation of valves 35 may be staggered, thus progressively freezing the tissue one portion at a time. If it becomes necessary to reduce the rate of freezing, one or more hoses 37 may be turned off or the rate of cryogen flow may be adjusted through valves 8 and 9. Additionally, if it becomes necessary to change a cylinder 22 during the procedure, only the valve 8 or 9 controlling the feed from the appropriate coupling 5 or 6 need be closed while the cylinder is changed.

The above embodiments and drawings illustrate the preferred embodiments of the present invention and it is understood that many variations and modifications of those embodiments will be evident to those skilled in the art and may be carried out without departing from the spirit and scope of the present invention.

What is claimed is:

1. A hand held cryogenic apparatus comprising a body of thermally insulative material having a first coupling for quickly connecting and disconnecting to a first source of cryogen, a second coupling for quickly connecting and disconnecting to a second source of cryogen, a cryoprobe member having means to receive and circulate there through cryogen from said first and second sources, a third coupling for quickly connecting and disconnecting to said cryoprobe member, a first flow passageway extending from said first coupling and a second flow passageway extending from said second coupling, said first and second flow passageways joining adjacent to said third coupling and connecting to said third coupling as a single passageway, said first and second flow passageways each having separately controllable valves therein, whereby said first and second flow passageways are adapted to convey cryogen from said first and second sources to said cryoprobe member and said valves are adapted to separately control the flow of cryogen from said first and second sources thereby providing individual flow of each fluid or combined flow thereof.

2. The apparatus of claim 1 further comprising a temperature sensing means positionable in combination with said cryoprobe member and a display means connected to said temperature sensing means.

3. The apparatus of claim 2 wherein said temperature sensing means comprises a thermocouple probe extendable from said body adjacent and parallel to said cryoprobe.

4. The apparatus of claim 2 wherein said temperature sensing means comprises a thermocouple on said cryoprobe having a detachable connection to said display means.

5. The apparatus of claim 1 further comprising a precharged container of cryogen having means cooperating with said first or second coupling and capable of being supported by said body.

6. The apparatus of claim 1 wherein said body is substantially elongated, said second and third couplings are positioned in substantial linear alignment at opposite ends of said body and are connected by said second flow passageway, and said first coupling is positioned parallel and adjacent to one surface of said body and wherein said first flow passageway connects said first coupling to said second flow passageway adjacent to said third coupling.

7. The apparatus of claim 6 which further comprises said first source of cryogen wherein said first source comprises a first precharged cylinder capable of connecting to and being supported by said first coupling.

8. The apparatus of claim 7 wherein said body further comprises a handle extending from said body substantially midway between said second and third coupling in a direction opposite to the location of said first coupling.

9. The apparatus of claim 8 wherein said second source of cryogen is remote from said apparatus and wherein said second coupling is adapted to be connected to said second source via a hose.

10. The apparatus of claim 8 which further comprises said second source of cryogen and wherein said second source comprises a second precharged cylinder capable of connecting to and being supported by said second coupling.

11. The apparatus of claim 1 further comprising a multiple probe adapter member mountable to said third coupling and having means to convey cryogen to a plurality of cryoprobes.

12. The apparatus of claim 11 wherein said adapter member comprises a manifold housing having a coupling cooperating with said third coupling and having a single inlet receiving cryogen from said body, a plurality of hoses leading from said manifold housing wherein each hose is provided with a cryoprobe, and a manifold structure within said manifold housing connecting said single inlet to each of said plurality of hoses, whereby cryogen flowing into said manifold housing from said body may be divided between each of said hoses.

13. The apparatus of claim 12 wherein said manifold structure of said adapter member further comprises independently operable flow control means for each hose.

14. A portable cryosurgical probe system comprising:

a hand held cryoprobe apparatus comprising an elongated body having on one end thereof a cryoprobe coupling member for changeably mounting a cryoprobe member, a first coupling for removably mounting a container of cryogen along one elongated side of said elongated body, a second coupling for removably connecting said cryoprobe apparatus to a second source of cryogen on an end of said elongated body opposite said one end, a handle extending away from said body along an elongated side of said elongated body opposite said one elongated side, flow passageways within said elongated body to convey cryogen from said container to said cryoprobe member and from said second source of cryogen to said cryoprobe member, and control valves in combination with said flow passageways to control flow of cryogen through said cryoprobe apparatus;

at least one container of cryogen removably mountable to said first coupling on said elongated body; and at least one cryoprobe member removably mountable to said cryoprobe coupling member to receive cryogen flow;

whereby cryogen may be introduced to said cryoprobe coupling member from said container or from said second source or simultaneously therefrom and whereby said container is removable from said body and replaceable while said system is in use.

15. The cryosurgical probe system of claim 14 comprising a plurality of cryoprobe members of different sizes.

16. The cryosurgical probe system of claim 14 further comprising a multiple probe adapter member mountable to said cryoprobe coupling member and having means to convey cryogen to a plurality of cryoprobe members.

17. The cryosurgical probe system of claim 16 wherein said adapter member comprises a manifold housing having a coupling cooperating with said cryoprobe coupling member and having a single inlet for receiving cryogen from said elongated body, a plurality of hoses leading from said housing wherein each hose is provided with a cryoprobe member, and a manifold structure within said manifold housing connecting said single inlet to each of said plurality of hoses, whereby cryogen flowing into said manifold housing from said elongated body may be divided between each of said hoses.

18. A method of conducting a cryosurgical procedure on selected tissue in the human body using a hand held, self-contained cryosurgical apparatus comprising, providing said hand-held cryosurgical apparatus comprising a body of thermally insulative material having a first coupling for quickly connecting and disconnecting to a first source of cryogen, a second coupling for quickly connecting and disconnecting to a second source of cryogen, a third coupling for quickly connecting and disconnecting to a cryoprobe member, a first flow passageway extending from said first coupling and a second flow passageway extending from said second coupling, said first and second flow passageways joining adjacent to said third coupling and connecting to said third coupling as a single passageway, said first and second flow passageways each having separately controllable valves therein, and a cryoprobe member connectable to said third coupling and having means to receive and circulate said cryogens therethrough;

whereby said first and second flow passageways are adapted to convey cryogen from said first and second sources to said cryoprobe member and said valves are adapted to separately control the flow of cryogen from each of said first and second sources to thereby provide individual flow of cryogen from either said first or said second source or combined flow thereof;

providing a cryoprobe member and mounting said member to said cryosurgical apparatus via said third coupling;

providing a cylinder of pressurized cryogen, said cylinder having a body and a neck portion wherein said neck portion has a structure to cooperatively seal with said first coupling and connecting said cylinder to said first coupling whereby said cylinder comprises said first source of cryogen and whereby said cylinder is sized to be removably supported by said cryosurgical apparatus;

positioning said cryoprobe member at said selected tissue and activating said valve in said first flow passageway to cause cryogen to flow from said cylinder into said cryoprobe member and to generate freezing temperatures therein, said freezing temperature being transferred to said tissue, and continuing said procedure until cryogen in said container is depleted and connecting at least one new source of cryogen to at least one of said first and second coupling to thereby allow said procedure to continue uninterrupted until said tissue is destroyed.

* * * * *